(12) United States Patent
Chung et al.

(10) Patent No.: US 8,362,276 B2
(45) Date of Patent: Jan. 29, 2013

(54) BETA-SULFONE IMIDES AND PREPARATION THEREOF

(75) Inventors: Kwang-Choon Chung, Kyeongki-do (KR); Hyun-Nam Cho, Kyeongki-do (KR); Myoung-Seon Gong, Seoul (KR); Yun-Ho Jung, Seoul (KR)

(73) Assignee: INKTEC Co., Ltd., Ansan (KR)

( * ) Notice: Subject to any disclaimer, the term of this patent is extended or adjusted under 35 U.S.C. 154(b) by 949 days.

(21) Appl. No.: 11/910,849

(22) PCT Filed: Apr. 5, 2006

(86) PCT No.: PCT/KR2006/001262
§ 371 (c)(1),
(2), (4) Date: May 28, 2008

(87) PCT Pub. No.: WO2006/107175
PCT Pub. Date: Oct. 12, 2006

(65) Prior Publication Data
US 2008/0262243 A1    Oct. 23, 2008

(30) Foreign Application Priority Data
Apr. 6, 2005 (KR) .......................... 10-2005-0028471

(51) Int. Cl.
 C07D 207/408 (2006.01)
 C07D 209/56 (2006.01)
 C07D 403/12 (2006.01)
 C07D 487/06 (2006.01)
(52) U.S. Cl. ............ 548/426; 546/68; 546/98; 546/188; 548/520; 548/521; 548/522; 548/547

(58) Field of Classification Search .................. None
See application file for complete search history.

(56) References Cited

U.S. PATENT DOCUMENTS

| | | | |
|---|---|---|---|
| 2,628,963 A | 2/1953 | Laucius et al. | |
| 2,753,356 A | 7/1956 | Laucius et al. | |
| 3,429,947 A * | 2/1969 | Van Eygen et al. | 525/113 |
| 4,596,863 A | 6/1986 | Sackmann et al. | |
| 5,290,497 A | 3/1994 | Kurita et al. | |
| 5,637,702 A * | 6/1997 | Patsch et al. | 544/3 |
| 6,437,009 B1 | 8/2002 | Meier et al. | |

FOREIGN PATENT DOCUMENTS

| JP | 49011154 A | 3/1974 |
|---|---|---|
| JP | 2000038373 A | 2/2000 |

OTHER PUBLICATIONS

Russo, Mario et al., "New Polyimides via Hyddrogen-Transfer Polymerization", Journal of Polymer Science: Part A-1, 7, 3337-3349, 1969.*

F. Barrow & R. G. Atkinson, "The Resolution of Inactive Alcohols by Means of their Esters with Tartranilic Acid." 1939, pp. 638-640, London,England.

Michael A. Brodney & Albert Padwa, "Generation and Trapping of N-Acyliminium Ions Derived from Isomunchnone Cycloadducts. A Versatile Route to Functionalized Heterocycles." 1999, pp. 556-565, vol. 64 No. 2, J. Org. Chem., American Chemical Society.

* cited by examiner

*Primary Examiner* — Fiona T Powers
(74) *Attorney, Agent, or Firm* — The Webb Law Firm

(57) ABSTRACT

The present invention provides a novel β-sulfonimide compound having at least one imide group and at least one sulfonyl group and a method for preparing the same.

14 Claims, 3 Drawing Sheets

【Fig. 1】
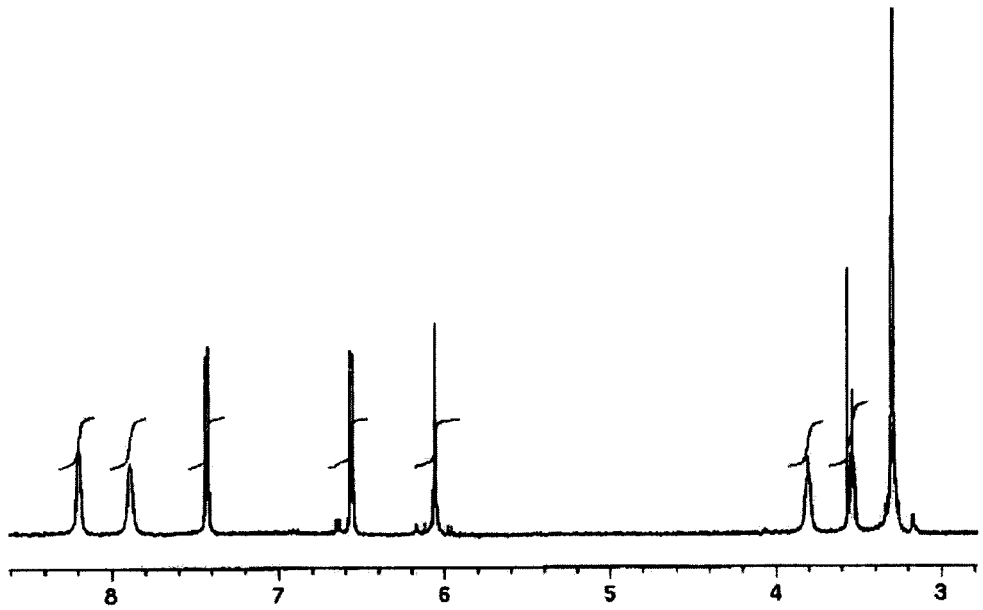
【Fig. 2】
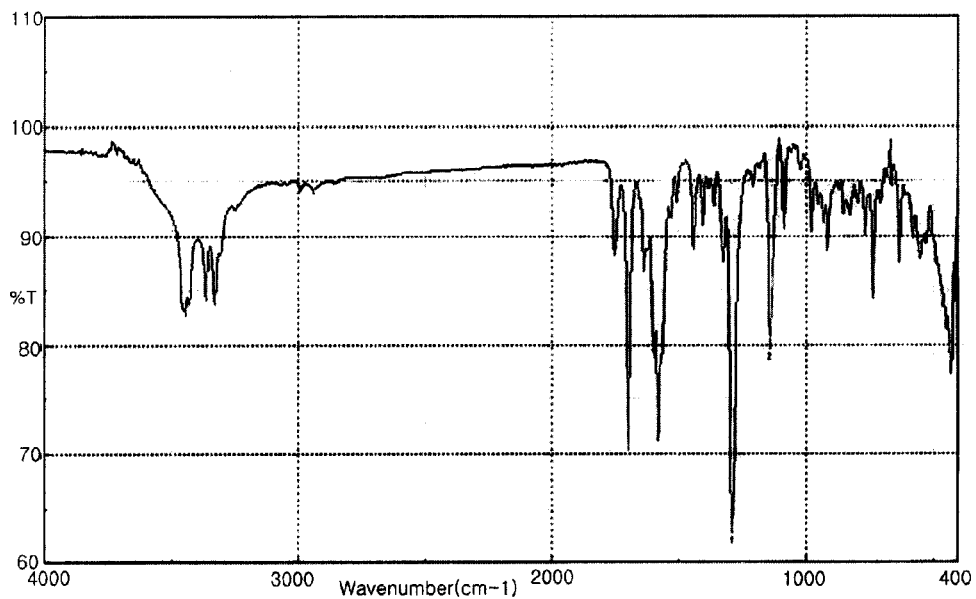

[Fig. 3]
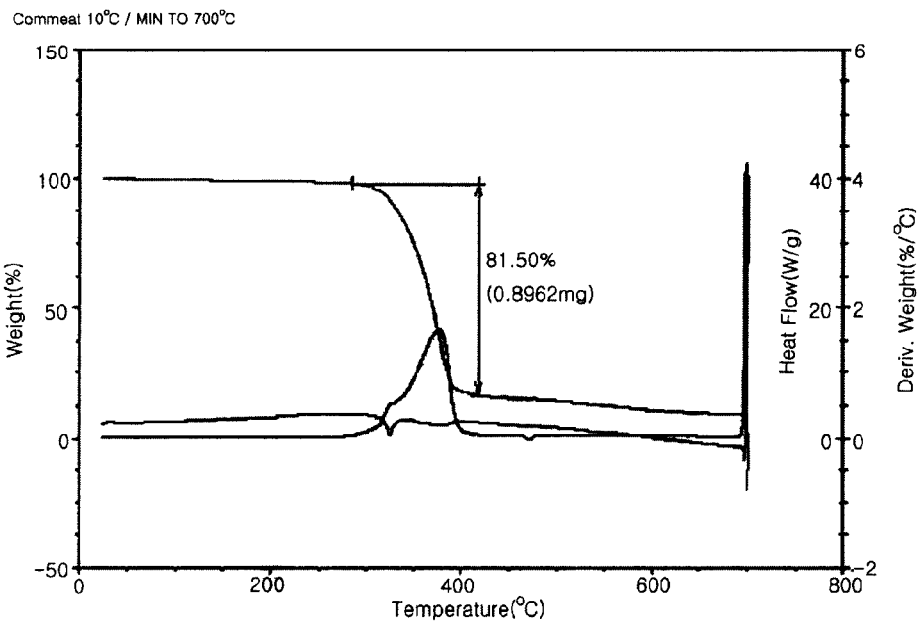
[Fig. 4]
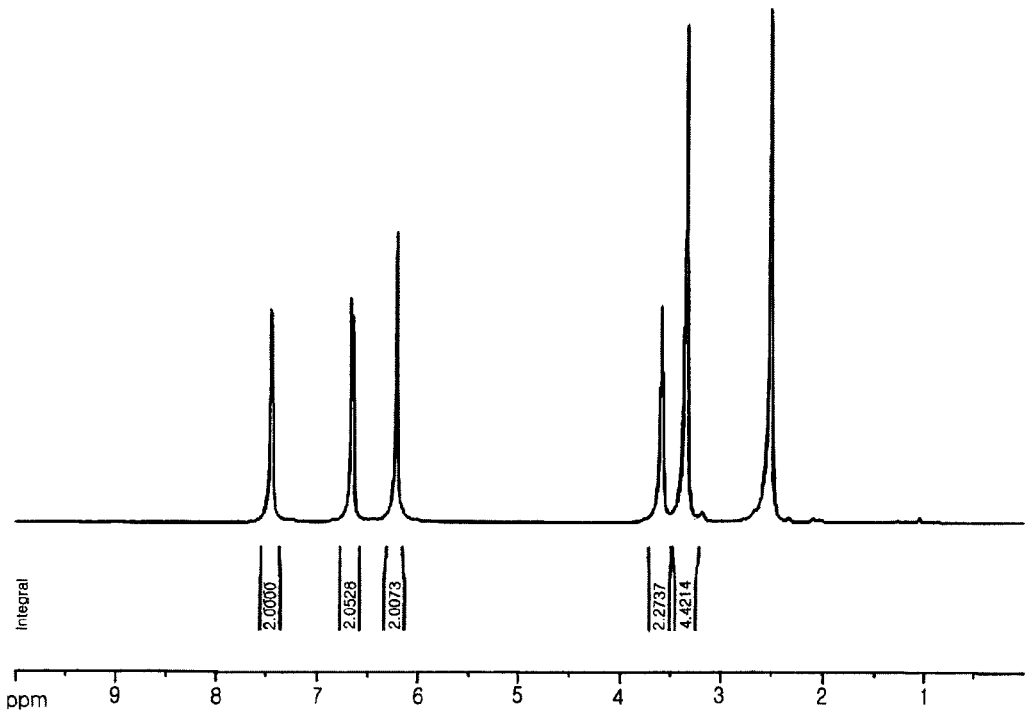

【Fig. 5】
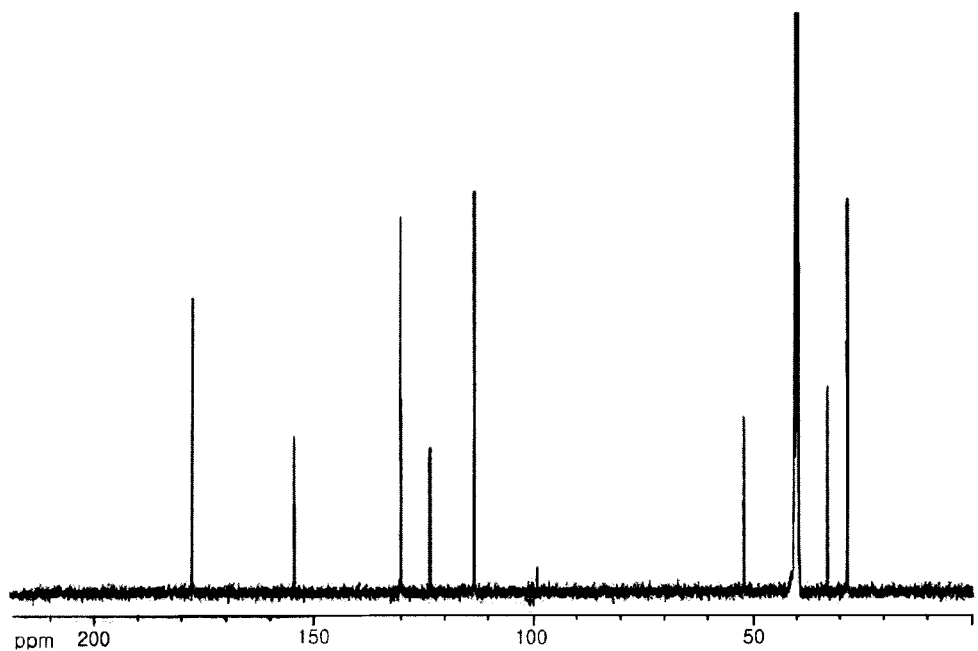
【Fig. 6】
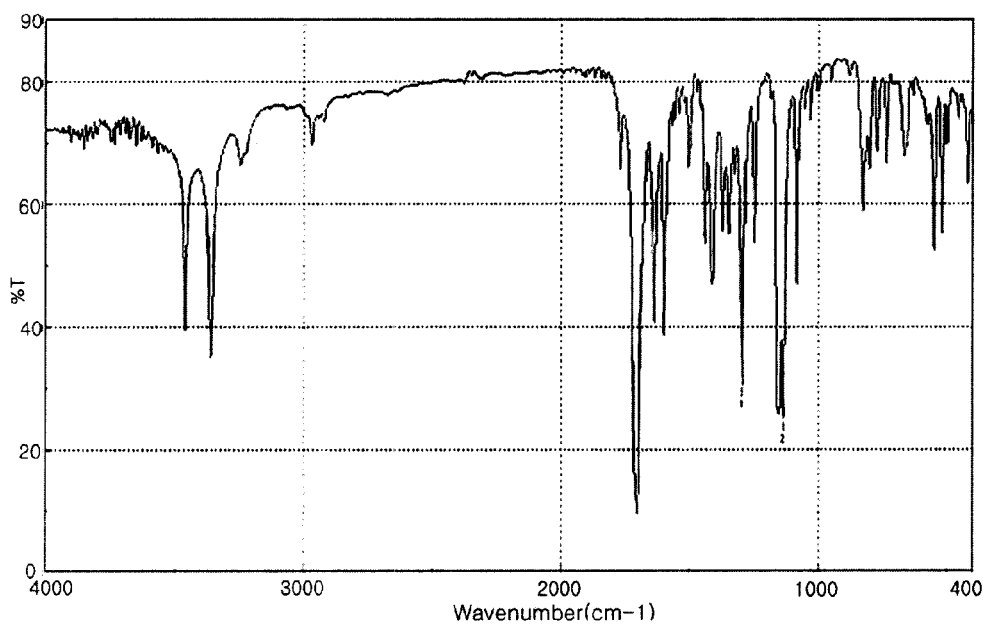

BETA-SULFONE IMIDES AND PREPARATION THEREOF

TECHNICAL FIELD

The present invention relates to a novel β-sulfonimide compound and a preparation method thereof.

BACKGROUND ART

N-alkylimides find many uses in electrics/electronics, medicine, agrochemicals, dyes, pigments and surfactants and thus are being actively studied. And, a variety of imide derivatives including phthalimide, succinimide and maleimide are used in many applications. U.S. Pat. No. 4,596,863 disclosed a use of N-alkylimide copolymers as sizing agent. Recently, U.S. Pat. No. 6,437,009 disclosed a use as low foam wetting agent. The use of imide compounds is expanding from medicinal and electric/electronic industries to more diverse industry fields.

In general, N-alkylimide compounds may be prepared by such known methods as presented in F. Barrow [*J. Chem. Soc.* (London), p. 638 (1939)], i.e., by condensation of carboxylic acid and primary amine, condensation of carboxylic acid ester and primary amine or condensation of carboxylic acid anhydride and primary amine.

Also, N-alkylimide compounds can be prepared from imide, for example, by the methods presented in U.S. Pat. No. 2,628,963 and U.S. Pat. No. 2,753,356, in which carboxyimide and primary amine are reacted at high temperature and under high pressure.

Polyimides frequently used as electronics material may be prepared by the above method. But, synthetic polyimides are prepared by condensing polyamic acid precursor at high temperature because of difficulty in processing, as disclosed in U.S. Pat. No. 5,290,497.

But, the condensation requires high temperature or high pressure and the primary amine should have a high basicity. Because of these problems, efforts to develop various compounds were unsuccessful. Especially, β-sulfoneamine has to be used as primary amine to prepare β-sulfonimide. But, preparation of β-sulfonimide by the afore-mentioned process is difficult because β-sulfoneamine has a low basicity.

DISCLOSURE

Technical Problem

The present inventors studied ardently to solve these problems and succeeded in making the present invention.

An object of the present invention is to provide a novel β-sulfonimide compound that can be used in a variety of industrial fields.

Another object of the present invention is to provide an economical and efficient method for preparing a β-sulfonimide compound through a simple process.

Technical Solution

The present invention provides a novel β-sulfonimide compound having at least one imide group and at least one sulfonyl group and a method for preparing the same, more particularly a novel β-sulfonimide compound represented by the formula (1) or (2) below and a method for preparing the same:

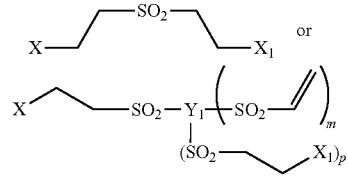 (1)

each of X and $X_1$ is, independently, selected from

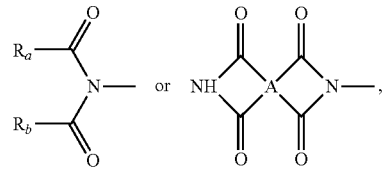

wherein each of $R_a$ and $R_b$ is, independently, selected from substituted or unsubstituted $C_1$-$C_{20}$ aliphatic, alicyclic or aromatic group and may or may not be connected with each other, A is $C_1$-$C_{20}$ substituted or unsubstituted aliphatic, aromatic or alicyclic group;

$Y_1$ is vinyl or $C_1$-$C_{20}$ substituted or unsubstituted aliphatic, aromatic or alicyclic group; and p and m are integers the sum of which ranges from 0 to 6 ($Y_1$ can be vinyl only when both p and m are 0);

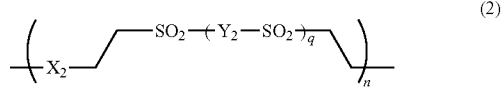 (2)

$X_2$ is

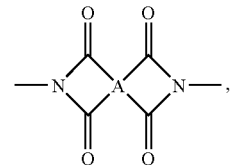

A is $C_1$-$C_{20}$ substituted or unsubstituted aliphatic, aromatic or alicyclic group, $Y_2$ is $C_1$-$C_{20}$ substituted or unsubstituted aliphatic, aromatic or alicyclic group, q is 0 or 1 and n is an integer 1 or larger.

In the formulas (1) and (2), the substituents may be independently selected from amine, nitro, aminoalkyl, aminoaryl, thiol, thioalkyl, thioaryl, hydroxy, oxyalkyl, oxyaryl, fluoro, chloro, bromo and iodo.

In the present invention, a β-sulfonimide compound is prepared by nucleophilic addition of a compound having at least one vinylsulfonyl group with a compound having at least one imide group in the presence of a proper catalyst.

Such nucleophilic addition is a Michael-type addition. As presented by A. Michael [*J. Prakt. Chem.* [2] 35, p. 349 (1987)], etc., a nucleophile is used as Michael donor and an activated unsaturated compound, for example, an α,β-unsaturated carbonyl compound, is used as Michael acceptor. In the present invention, imide is used as Michael donor and vinylsulfone is used as Michael acceptor. Particularly, the present invention is characterized in selectively using vinylsulfone as Michael acceptor.

To be specific, nucleophilic addition of an imide compound represented by the formula (3) below with a vinylsulfone compound represented by the formula (4) below is carried out in the presence of catalyst to prepare the β-sulfonimide compound represented by the formula (1) or (2):

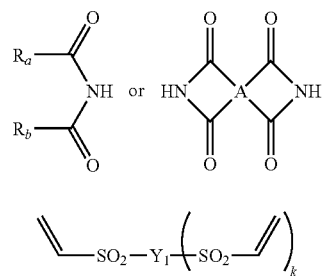
(3)

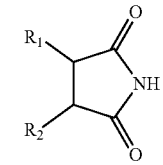
(4)

$R_a$, $R_b$, A and $Y_1$ are the same as defined above, k is an integer from 0 to 6 and $Y_1$ can be vinyl only when k is 0.

Specific, but non-restrictive examples of the compound resented by the formula (3) are given in the formulas (5) to (13) below:

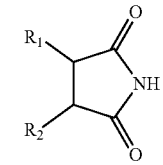
(5)

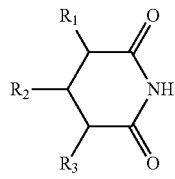
(6)

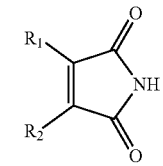
(7)

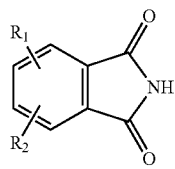
(8)

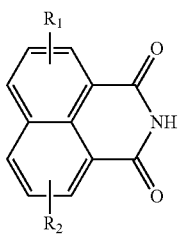
(9)

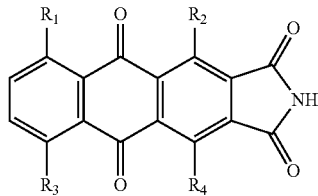
(10)

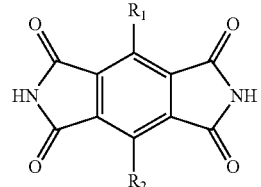
(11)

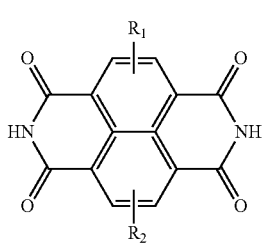
(12)

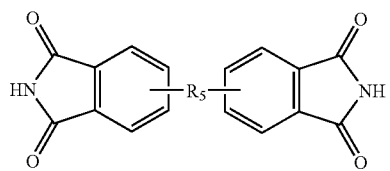
(13)

each of $R_1$ to $R_4$ may be identical or different and is a substituent independently selected from hydrogen, amine, nitro, aminoalkyl, aminoaryl, thiol, thioalkyl, thioaryl, hydroxy, oxyalkyl, oxyaryl, fluoro, chloro, bromo and iodo or $C_1$-$C_{20}$ aliphatic, aromatic or alicyclic group substituted by said substituent or unsubstituted and $R_5$ is $C_1$-$C_{20}$ alkyl, cycloalkyl or aromatic group substituted by said substituent or unsubstituted.

Specific, but non-restrictive examples of the compound resented by the formula (4) are given in the formulas (14) to (17) below, but any vinylsulfone compound having at least one vinyl group neighboring a sulfonyl group may be used in the present invention.

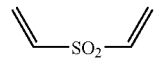
(14)

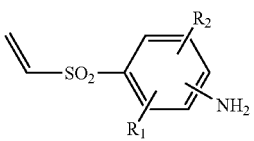
(15)

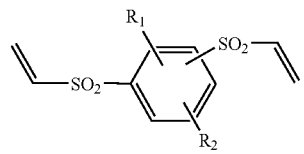
(16)

-continued

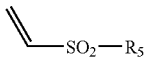
(17)

$R_1$, $R_2$ and $R_5$ are the same as defined above.

The solvent used in the present invention need not be particularly limited, but one capable of dissolving the reactants well is preferable. For example, ketones such as acetone and 2-butanone, ethers such as diethyl ether and dioxane and amides such as N,N-dimethylformamide, N,N-dimethylacetamide and N-methylpyrrolidone may be used.

The catalyst used in the present invention need not be particularly limited, as long as the objects of the present invention can be attained. That is, any catalyst can be used, as long as the compound provided by the present invention is obtained. In general, organic bases such as benzyltrimethylammonium hydroxide, dimethyldiethylammonium hydroxide, ethyltrimethylammonium hydroxide, methyltriethylammonium hydroxide, tetrabutylammonium hydroxide, tetrabutylphosphonium hydroxide, tetraethylammonium hydroxide, tetramethylammonium hydroxide and tetrapropylammonium hydroxide may be used as catalyst. The content of the catalyst need not be particularly limited, but it is preferably used within 0.1-20 wt %, more preferably within 1-15 wt %, based on the weight of the reactants.

In the preparation method according to the present invention, the reaction temperature may be adjusted depending on the particular solvent used. Usually, 20-100° C. is preferred and 40-80° C. is more preferred.

In the preparation method of the present invention, separation and purification of the β-sulfonimide compound may be carried out by common techniques, including column chromatography, distillation, recrystallization, etc. However, it is simple and convenient to precipitate the β-sulfonimide compound using alcohols such as methanol, ethanol and propanol.

DESCRIPTION OF DRAWINGS

FIG. 1 is the $^1$H-NMR spectrum of the β-sulfonimide compound prepared in Example 1.

FIG. 2 is the IR spectrum of the β-sulfonimide compound prepared in Example 1.

FIG. 3 is the thermal analysis (DSC-TGA) spectrum of the β-sulfonimide compound prepared in.

FIG. 4 is the $^1$H-NMR spectrum of the β-sulfonimide compound prepared in Example 2.

FIG. 5 is the $^{13}$C-NMR spectrum of the β-sulfonimide compound prepared in Example 2.

FIG. 6 is the IR spectrum of the β-sulfonimide compound prepared in Example 2.

BEST MODE

Hereinafter, the embodiments of the present invention will be described in detail through examples. However, it will be appreciated that those skilled in the art, in consideration of this disclosure, may make modifications and improvements within the spirit and scope of the present invention.

Example 1

Preparation of 1,4-diaminoanthraquinone-(N-anilinesulfonylethyl)-2,3-dicarboxylmide In a 500 mL round bottom flask, a mixture of 20 g of 1,4-diaminoanthraquinone-2,3-dicarboxylmide, 12.5 g of 4-ethenesulfonylphenylamine and 200 g of 1,4-dioxane was heated to 40-50° C. and stirred. To the reaction solution was added 4.3 g of 40% aqueous tetrabutylammonium hydroxide solution 3 times over a 1-hour period. Subsequently, the mixture was stirred at 40-50° C. for 6 more hours. After stopping to stir, the reaction solution was cooled to room temperature and precipitated and dispersed in 1 L of methanol. The resultant precipitate was filtered, redispersed in 1 L of clean water, filtered again and washed to remove salt. Then, the product was redispersed in 500 mL of methanol, filtered and dried to obtain 31 g of 1,4-diaminoanthraquinone-(N-anilinesulfonylethyl)-2,3-dicarboxylmide (yield=97%).

IR (KBr): $v_{max}$=1290.1 cm$^{-1}$, 1143.6 cm$^{-1}$ (—SO$_2$—)

$^1$H-NMR (DMSO-d$_6$) δ (ppm): 8.2 (2H, d, ArH), 7.9 (2H, t, ArH) 7.4 (2H, d, ArH), 6.5 (2H, d, ArH), 3.8 (2H, t, —CH$_2$SO$_2$—), 3.5 (2H, t, —N$_{(imide)}$CH$_2$—)

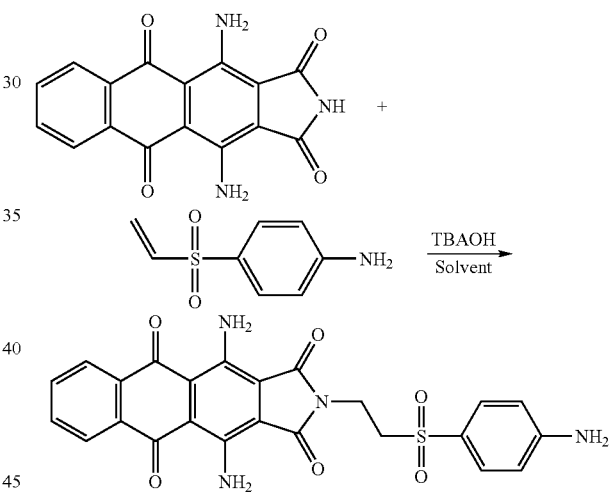

Example 2

Preparation of 1-[2-(4-amino-benzenesulfonyl)-ethyl]-pyrrolidine-2,5-dione

In a 100 mL round bottom flask, a mixture of 1.15 g of succinimide, 2 g of 4-ethenesulfonylphenylamine and 30 g of 1,4-dioxane was heated to 60-70° C. and stirred. To the reaction solution was added 0.75 g of 40% aqueous tetrabutylammonium hydroxide solution 3 times over a 1-hour period. Subsequently, the mixture was stirred at 60-70° C. for 2 more hours. When the solution turned into a white suspension, stirring was stopped and the reaction solution was cooled to room temperature and precipitated and dispersed in 100 mL of methanol. The resultant precipitate was filtered, redispersed in 100 mL of clean water, filtered again and washed to remove salt. Then, the product was redispersed in 500 mL of methanol, filtered and dried to obtain 2.2 g of 1-

[2-(4-amino-benzenesulfonyl)-ethyl]-pyrrolidine-2,5-dione (yield=70%).

IR (KBr): $v_{max}$=1294.9 cm$^{-1}$, 1138.7 cm$^{-1}$ (—SO$_2$—)

$^1$H-NMR (DMSO-d$_6$) δ (ppm): 7.4 (2H, d, ArH), 6.6 (2H, d, ArH) 6.2 (2H, d, NH$_2$), 3.6 (2H, t, —CH$_2$SO$_2$—), 3.3 (2H, t, —N(imide)CH$_2$—), 2.5 (4H, t, —CH$_2$CH$_2$—)

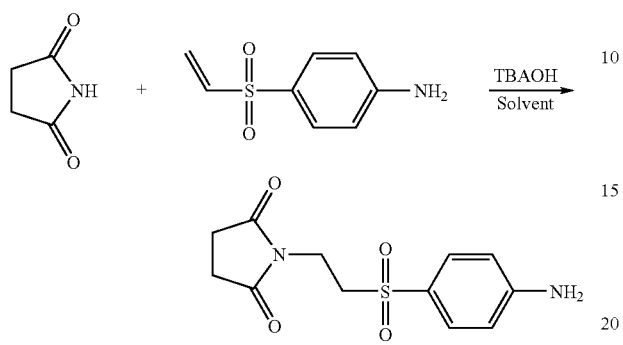

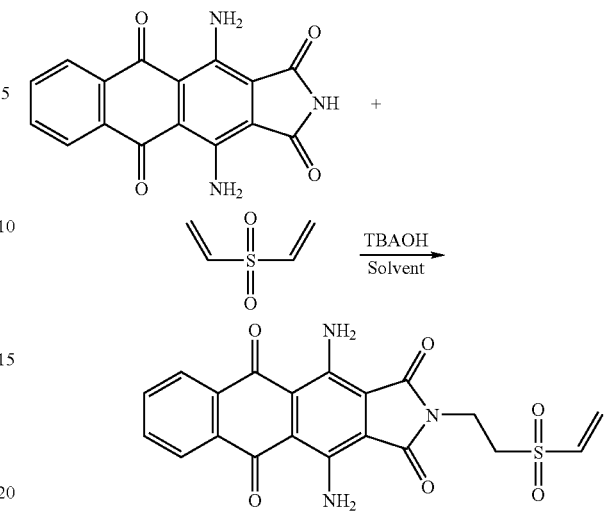

Example 3

Preparation of 1,4-diaminoanthraquinone-(N-vinyl-sulfonylethyl)-2,3-dicarboxylmide In a 1 L round bottom flask, a mixture of 50 g of 1,4-diaminoanthraquinone-2,3-dicarboxylmide, 21 g of divinylsulfone and 400 g of 1,4-dioxane was heated to 40-50° C. and stirred. To the reaction solution was added 11 g of 40% aqueous tetrabutylammonium hydroxide solution 3 times over a 1-hour period. Subsequently, the mixture was stirred at 40-50° C. for 5 more hours. After stopping stirring, the reaction solution was cooled to room temperature and precipitated and dispersed in 1 L of methanol. The resultant precipitate was filtered, redispersed in 100 mL of clean water, filtered again and washed to remove salt. Then, the product was redispersed in 1 L of methanol, filtered and dried to obtain 66 g of 1,4-diaminoanthraquinone-(N-vinylsulfonylethyl)-2,3-dicarboxylmide (yield=95%).

IR (KBr): $v_{max}$=1290.1 cm$^{-1}$, 1132.9 cm$^{-1}$ (—SO$_2$—)

$^1$H-NMR (DMSO-d$_6$) δ (ppm): 8.2 (2H, d, ArH), 7.0 (1H, m, —CH=) 6.3 (2H, dd, =CH$_2$), 3.5 (2H, t, —CH$_2$SO$_2$—), 3.3 (2H, t, —N$_{(imide)}$CH$_2$—)

Example 4

Preparation of bis(1,4-diaminoanthraquinone-(N-ethyl)-2,3-dicarboxylmide)sulfone In a 100 mL round bottom flask, a mixture of 2 g of 1,4-diaminoanthraquinone-2,3-dicarboxylmide, 0.39 g of divinylsulfone and 15 g of 1,4-dioxane was heated to 40-50° C. and stirred. To the reaction solution was added 0.43 g of 40% aqueous tetrabutylammonium hydroxide solution. Subsequently, the mixture was stirred at 50-60° C. for 4 more hours. After stopping stirring, the reaction solution was cooled to room temperature and precipitated and dispersed in 100 mL of methanol. The resultant precipitate was filtered, redispersed in 100 mL of clean water, filtered again and washed to remove salt. Then, the product was redispersed in 50 mL of methanol, filtered and dried to obtain 2.1 g of bis(1,4-diaminoanthraquinone-(N-ethyl)-2,3-dicarboxylmide)sulfone (yield=87%).

IR (KBr): $v_{max}$=1290.1 cm$^{-1}$, 1125.3 cm$^{-1}$ (—SO$_2$—).

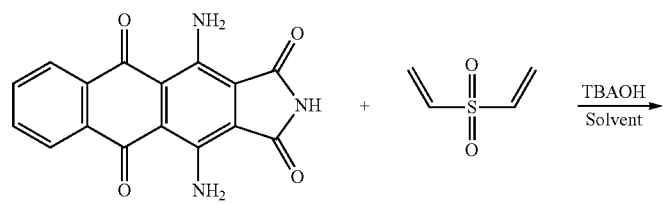

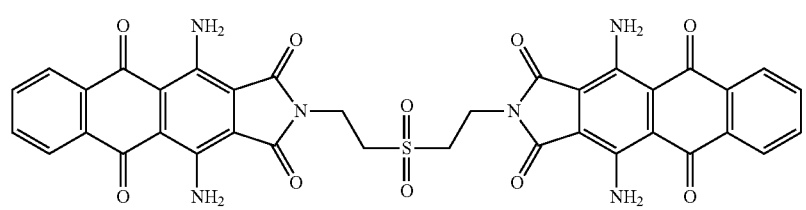

Example 5

Preparation of bis(1,4-diaminoanthraquinone-(N-ethyl)-2,3-dicarboxylmide)sulfone In a 100 mL round bottom flask, a mixture of 2 g of 1,4-diaminoanthraquinone-(N-vinylsulfonylethyl)-2,3-dicarboxylmide, 1.44 g of 1,4-diaminoanthraquinone-2,3-dicarboxylmide and 20 g of 1,4-dioxane was heated to 40-50° C. and stirred. To the reaction solution was added 0.3 g of 40% aqueous tetrabutylammonium hydroxide solution. Subsequently, the mixture was stirred at 50-60° C. for 3 more hours. After stopping stirring, the reaction solution was cooled to room temperature and precipitated and dispersed in 100 mL of methanol. The resultant precipitate was filtered, redispersed in 100 mL of clean water, filtered again and washed to remove salt. Then, the product was redispersed in 50 mL of methanol, filtered and dried to obtain 2.95 g of bis(1,4-diaminoanthraquinone-(N-ethyl)-2,3-dicarboxylmide)sulfone (yield=86%).

IR (KBr): $v_{max}$=1290.1 cm$^{-1}$, 1125.3 cm$^{-1}$ (—SO$_2$—)

Example 6

Preparation of 1,4-diaminoanthraquinone-(N-succinimidylethanesulfonylethyl)-2,3-dicarboxylmide In a 100 mL round bottom flask, a mixture of 0.47 g of succinimide, 2 g of 1,4-diaminoanthraquinone-(N-vinylsulfonylethyl)-2,3-dicarboxylmide and 20 g of 1,4-dioxane was heated to 40-50° C. and stirred. To the reaction solution was added 0.3 g of 40% aqueous tetrabutylammonium hydroxide solution. Subsequently, the mixture was stirred at 50-60° C. for 3 more hours. After stopping stirring, the reaction solution was cooled to room temperature and precipitated and dispersed in 100 mL of methanol. The resultant precipitate was filtered, redispersed in 100 mL of clean water, filtered again and washed to remove salt. Then, the product was redispersed in 50 mL of methanol, filtered and dried to obtain 2.17 g of 1,4-diaminoanthraquinone-(N-succinimidylethanesulfonylethyl)-2,3-dicarboxylmide (yield=88%).

IR (KBr): $v_{max}$=1292.1 cm$^{-1}$, 1124.3 cm$^{-1}$ (—SO$_2$—)

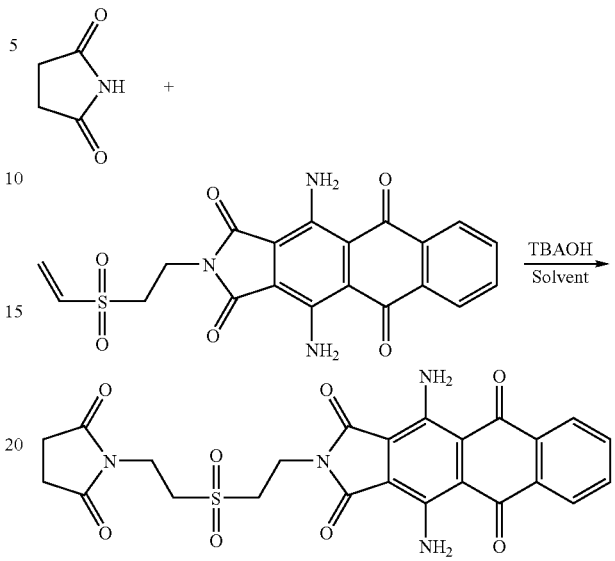

Example 7

Preparation of poly(β-sulfone-imide)

In a 100 mL round bottom flask, a mixture of 1 g of pyromellitic diimide, 0.55 g of divinylsulfone and 20 g of N,N-dimethylacetamide was heated to 40-50° C. and stirred. To the reaction solution was added 0.58 g of 40% aqueous tetrabutylammonium hydroxide solution. Subsequently, the mixture was stirred at 40-50° C. for 12 more hours. After stopping stirring, the reaction solution was cooled to room temperature and precipitated and dispersed in 100 mL of methanol. The resultant precipitate was filtered, redispersed in methanol, filtered again and washed to remove salt. Then, the product was dried to obtain 1.44 g of poly(β-sulfone-imide) (yield=93%).

IR (KBr): $v_{max}$=1304.6 cm$^{-1}$, 1132.0 cm$^{-1}$ (—SO$_2$—)

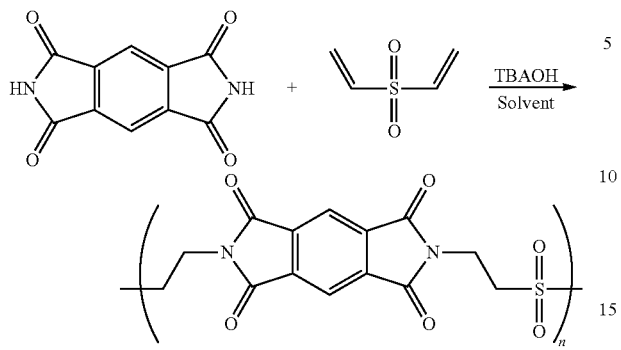

Example 8

Preparation of N-vinylsulfonylethylmaleimide

In a 50 mL round bottom flask, a mixture of 0.5 g of maleimide, 0.61 g of divinylsulfone and 10 g of 1,4-dioxane was heated to 40-50° C. and stirred. To the reaction solution was added 0.67 g of 40% aqueous tetrabutylammonium hydroxide solution. Subsequently, the mixture was stirred at 40-50° C. for 3 more hours. After stopping stirring, the reaction solution was cooled to room temperature and precipitated and dispersed in 100 mL of methanol. The resultant precipitate was filtered, redispersed in a large volume of clean water, filtered again and washed to remove salt. Then, the product was redispersed in 50 mL of methanol, filtered and dried to obtain 0.94 g of N-vinylsulfonylethylmaleimide (yield=61%)

IR (KBr): $v_{max}$=1305.6 cm$^{-1}$, 1127.2 cm$^{-1}$ (—SO$_2$—)

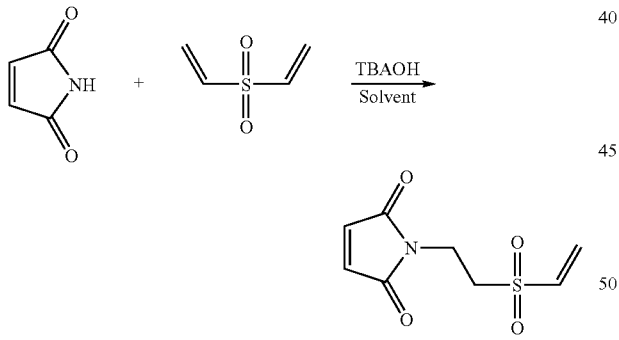

Example 9

Preparation of bis(N-maleimidylethyl)sulfone

In a 50 mL round bottom flask, a mixture of 1.0 g of maleimide, 0.61 g of divinylsulfone and 20 g of 1,4-dioxane was heated to 40-50° C. and stirred. To the reaction solution was added 1.2 g of 40% aqueous tetrabutylammonium hydroxide solution little by little. Subsequently, the mixture was stirred at 40-50° C. for 5 more hours. After stopping stirring, the reaction solution was cooled to room temperature and precipitated and dispersed in 100 mL of methanol. The resultant precipitate was filtered, redispersed in a large volume of clean water, filtered again and washed to remove salt. Then, the product was redispersed in 100 mL of methanol, filtered and dried to obtain 1.32 g of bis(N-maleimidylethyl)sulfone (yield=70%).

IR (KBr): $v_{max}$=1305.6 cm$^{-1}$, 1127.2 cm$^{-1}$ (—SO$_2$—)

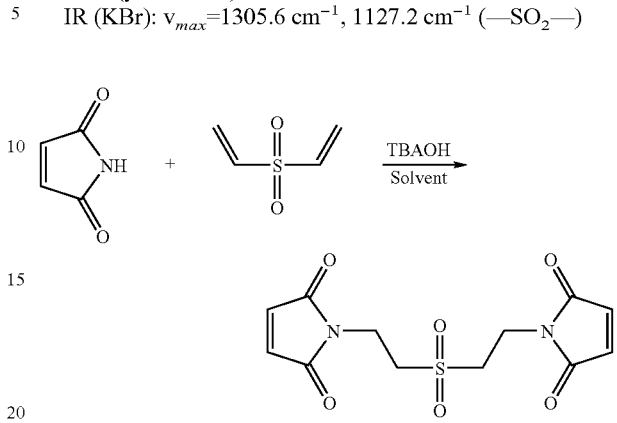

INDUSTRIAL APPLICABILITY

In accordance with the present invention, novel β-sulfonimide compounds with wanted properties can be prepared simply and in good yield by selective reaction with imide group and vinylsulfone group. The β-sulfonimide compounds provided by the present invention can be utilized in a variety of applications, including medicine, dyes, pigments, agrochemicals, polymer compounds and electric/electronic materials.

Those skilled in the art will appreciate that the concepts and specific embodiments disclosed in the foregoing description may be readily utilized as a basis for modifying or designing other embodiments for carrying out the purposes of the present invention. Those skilled in the art will also appreciate that such equivalent embodiments do not depart from the spirit and scope of the present invention as set forth in the appended claims.

The invention claimed is:

1. A β-sulfonimide compound represented by the following formula (1) or (2):

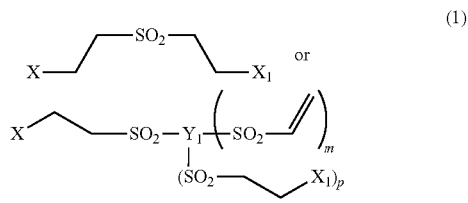

wherein, in the formula (1), each of X and X$_1$ is, independently, selected from

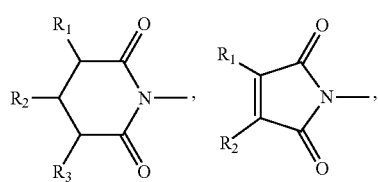

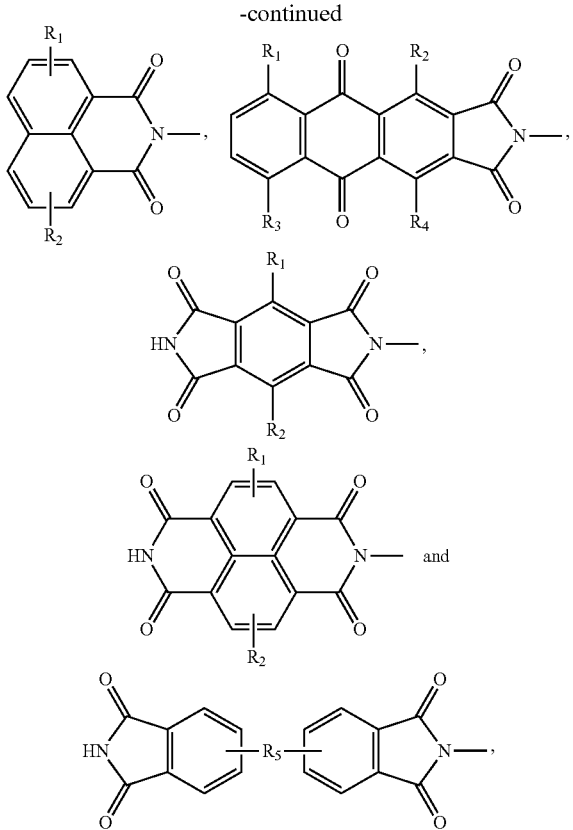

wherein each of $R_1$ to $R_4$ may be identical or different and is a substituent independently selected from hydrogen, amine, nitro, aminoalkyl, aminoaryl, thiol, thioalkyl, thioaryl, hydroxy, oxyalkyl, oxyaryl, fluoro, chloro, bromo and iodo or $C_1$-$C_{20}$ aliphatic, aromatic or alicyclic group substituted by said substituent or unsubstituted and $R_5$ is $C_1$-$C_{20}$ alkyl, cycloalkyl or aromatic group substituted by said substituent or unsubstituted;

$Y_1$ is vinyl or $C_1$-$C_{20}$ substituted or unsubstituted aliphatic, aromatic or alicyclic group; and p and m are integers the sum of which ranges from 0 to 6 ($Y_1$ can be vinyl only when both p and m are 0);

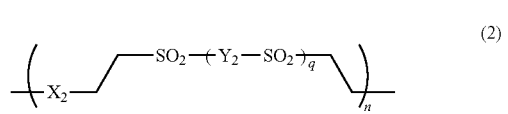

$X_2$ is

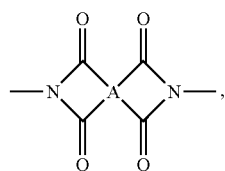

A is $C_1$-$C_{20}$ substituted or unsubstituted aliphatic, aromatic or alicyclic group, $Y_2$ is $C_1$-$C_{20}$ substituted or unsubstituted aliphatic, aromatic or alicyclic group, q is 0 or 1 and n is an integer 1 or larger.

2. The β-sulfonimide compound as set forth in claim 1, wherein, in the formula (2), the substituents are at least one selected from amine, nitro, aminoalkyl, aminoaryl, thiol, thioalkyl, thioaryl, hydroxy, oxyalkyl, oxyaryl, fluoro, chloro, bromo and iodo.

3. The β-sulfonimide compound as set forth in claim 1, wherein, in the formula (2), $X_2$ is selected from

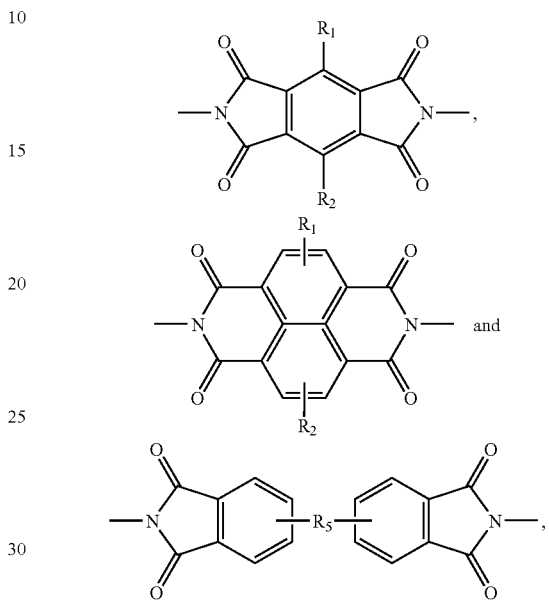

where each $R_1$ and $R_2$ may be identical or different and is a substituent independently selected from hydrogen, amine, nitro, aminoalkyl, aminoaryl, thiol, thioalkyl, thioaryl, hydroxy, oxyalkyl, oxyaryl, fluoro, chloro, bromo and iodo or $C_1$-$C_{20}$ aliphatic, aromatic or alicyclic group substituted by said substituent or unsubstituted and $R_5$ is $C_1$-$C_{20}$ alkyl, cycloalkyl or aromatic group substituted by said substituent or unsubstituted.

4. The β-sulfonimide compound as set forth in claim 1, wherein, in the formula (1), $Y_1$ is selected from

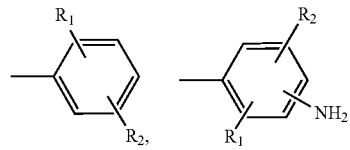

and —$R_5$, where each $R_1$ and $R_2$ may be identical or different and is a substituent independently selected from hydrogen, amine, nitro, aminoalkyl, aminoaryl, thiol, thioalkyl, thioaryl, hydroxy, oxyalkyl, oxyaryl, fluoro, chloro, bromo and iodo or $C_1$-$C_{20}$ aliphatic, aromatic or alicyclic group substituted by said substituent or unsubstituted and $R_5$ is $C_1$-$C_{20}$ alkyl, cycloalkyl or aromatic group substituted by said substituent or unsubstituted.

5. A method for preparing a β-sulfonimide compound represented by the following formula (1) or (2) by nucleophilic addition of an imide compound represented by the following formula (3) with a vinylsulfone compound represented by the following formula (4) in the presence of catalyst:

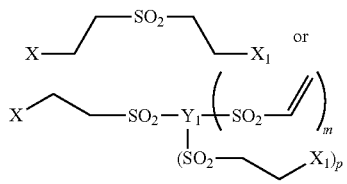
(1)

wherein, in the formula (1), each of X and $X_1$ is, independently, selected from

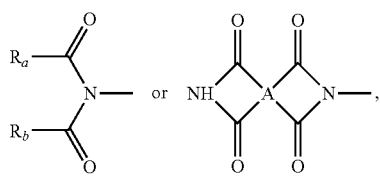

wherein each of $R_a$ and $R_b$ is, independently, selected from substituted or unsubstituted $C_1$-$C_{20}$ aliphatic, alicyclic or aromatic group and may or may not be connected with each other, A is $C_1$-$C_{20}$ substituted or unsubstituted aliphatic, aromatic or alicyclic group;

$Y_1$ is vinyl or $C_1$-$C_{20}$ substituted or unsubstituted aliphatic, aromatic or alicyclic group; and p and m are integers the sum of which ranges from 0 to 6 ($Y_1$ can be vinyl only when both p and m are 0);

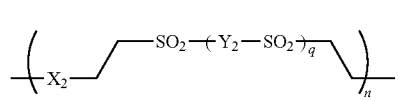
(2)

wherein, in the formula (2), $X_2$ is

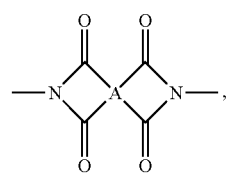

A is $C_1$-$C_{20}$ substituted or unsubstituted aliphatic, aromatic or alicyclic group, $Y_2$ is $C_1$-$C_{20}$ substituted or unsubstituted aliphatic, aromatic or alicyclic group, q is 0 or 1 and n is an integer 1 or larger;

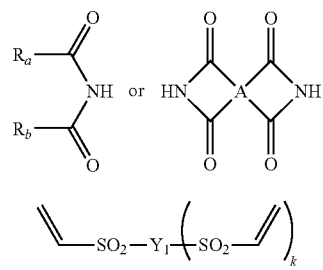
(3)

(4)

wherein, in the formula (3), each of $R_a$ and $R_b$ is, independently, selected from substituted or unsubstituted $C_1$-$C_{20}$ aliphatic, alicyclic or aromatic group and may or may not be connected with each other, A is $C_1$-$C_{20}$ substituted or unsubstituted aliphatic, aromatic or alicyclic group; and wherein, in the formula (4), $Y_1$ is vinyl or $C_1$-$C_{20}$ substituted or unsubstituted aliphatic, aromatic or alicyclic group and k is an integer from 0 to 6 and $Y_1$ can be vinyl only when k is 0.

6. The preparation method as set forth in claim 5, wherein the substituents are at least one selected from amine, nitro, aminoalkyl, aminoaryl, thiol, thioalkyl, thioaryl, hydroxy, oxyalkyl, oxyaryl, fluoro, chloro, bromo and iodo.

7. The preparation method as set forth in claim 5, wherein a solvent is further used in preparing the β-sulfonimide compound.

8. The preparation method as set forth in claim 7, wherein the solvent is at least one selected from the group consisting of ketone, ether and amide.

9. The preparation method as set forth in claim 5, wherein the catalyst is quaternary ammonium hydroxide.

10. The preparation method as set forth in claim 9, wherein the catalyst is selected from benzyltrimethylammonium hydroxide, dimethyldiethylammonium hydroxide, ethyltrimethylammonium hydroxide, methyltriethylammonium hydroxide, tetrabutylammonium hydroxide, tetrabutylphosphonium hydroxide, tetraethylammonium hydroxide, tetramethylammonium hydroxide and tetrapropylammonium hydroxide.

11. The preparation method as set forth in claim 5, wherein the preparation is carried out in a temperature range of 20-100° C.

12. The preparation method as set forth in claim 5, wherein the β-sulfonimide compound is collected using a nonsolvent.

13. The preparation method as set forth in claim 12, wherein the nonsolvent is selected from methanol, ethanol or propanol.

14. A β-sulfonimide compound represented by the following formula (1):

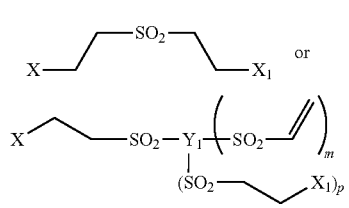
(1)

wherein, in the formula (1), X is

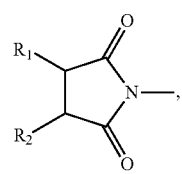

and $X_1$ is selected from

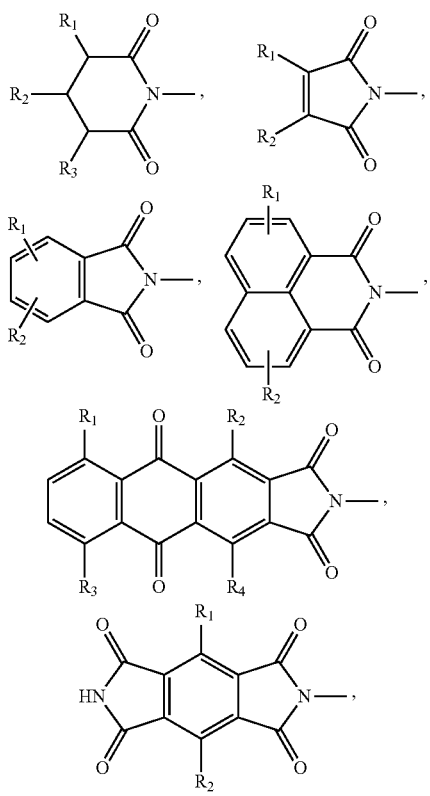

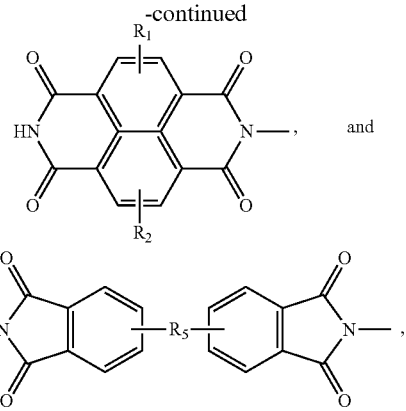

wherein each of $R_1$ to $R_4$ may be identical or different and is a substituent independently selected from hydrogen, amine, nitro, aminoalkyl, aminoaryl, thiol, thioalkyl, thioaryl, hydroxy, oxyalkyl, oxyaryl, fluoro, chloro, bromo and iodo or $C_1$-$C_{20}$ aliphatic, aromatic or alicyclic group substituted by said substituent or unsubstituted and $R_5$ is $C_1$-$C_{20}$ alkyl, cycloalkyl or aromatic group substituted by said substituent or unsubstituted;

$Y_1$ is vinyl or $C_1$-$C_{20}$ substituted or unsubstituted aliphatic, aromatic or alicyclic group; and p and m are integers the sum of which ranges from 0 to 6 ($Y_1$ can be vinyl only when both p and m are 0).

\* \* \* \* \*

UNITED STATES PATENT AND TRADEMARK OFFICE
CERTIFICATE OF CORRECTION

PATENT NO. : 8,362,276 B2
APPLICATION NO. : 11/910849
DATED : January 29, 2013
INVENTOR(S) : Kwang Choon Chung et al.

Page 1 of 1

It is certified that error appears in the above-identified patent and that said Letters Patent is hereby corrected as shown below:

Title of the Patent, item 56, Column 2, OTHER PUBLICATIONS, Line 1, delete "Hyddrogen-"
and insert -- Hydrogen- --

Column 14, Line 44, Claim 4, after "from" insert -- –CH=CH$_2$, --

Signed and Sealed this
Ninth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO.       : 8,362,276 B2
APPLICATION NO.  : 11/910849
DATED            : January 29, 2013
INVENTOR(S)      : Chung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1300 days.

Signed and Sealed this
First Day of September, 2015

Michelle K. Lee
*Director of the United States Patent and Trademark Office*